United States Patent
Ogisu et al.

(10) Patent No.: US 6,461,649 B1
(45) Date of Patent: Oct. 8, 2002

(54) IMPROVING QUALITY OF FLOUR-BAKED COMPOSITIONS

(75) Inventors: Akio Ogisu, Nagoya (JP); Kenji Hanno, Hirakata (JP)

(73) Assignee: Katayama Chemical, Inc., Osaka (JP)

( * ) Notice: Subject to any disclaimer, the term of this patent is extended or adjusted under 35 U.S.C. 154(b) by 0 days.

(21) Appl. No.: 09/545,866

(22) Filed: Apr. 7, 2000

(51) Int. Cl.⁷ .................................................. A21D 2/26
(52) U.S. Cl. ............................ 426/28; 426/64; 426/656
(58) Field of Search ........................ 426/549, 61, 622, 426/618, 653, 656, 18, 44, 46, 49, 52, 64, 28

(56) References Cited

U.S. PATENT DOCUMENTS

| | | | | |
|---|---|---|---|---|
| 3,694,221 A | * | 9/1972 | Hoer et al. ..................... | 99/17 |
| 5,138,038 A | | 8/1992 | Katayama et al. | |
| 5,273,773 A | | 12/1993 | Katayama et al. | |
| 5,274,079 A | | 12/1993 | Katayama et al. | |

FOREIGN PATENT DOCUMENTS

| | | | |
|---|---|---|---|
| DE | 04125972 | * | 2/1993 |
| DE | 4440958 | * | 5/1996 |
| EP | 0 298 419 | | 1/1989 |
| EP | 0 685 164 | | 12/1995 |
| EP | 0 867 116 | | 9/1998 |
| EP | 0 938 845 | | 9/1999 |
| JP | 59-088040 | | 5/1984 |
| JP | 64-014274 | | 1/1989 |
| JP | 6-091793 | | 11/1994 |
| JP | 0 81 69 816 | * | 7/1996 |
| JP | 2000-116312 | | 4/2000 |

* cited by examiner

Primary Examiner—Keith Hendricks
(74) Attorney, Agent, or Firm—Oblon, Spivak, McClelland, Maier & Neustadt, P.C.

(57) ABSTRACT

The present invention provides a composition for the improvement of the quality of a flour-baked composition such as bread and sponge cake, which comprises, (a) 0.005 to 2 parts by weight of a cereal protein partial decomposition product having a weight average molecular weight (Mw) of about 5,000 to about 90,000, and (b) 1 to 1,500 units of at least one enzyme selected from an amylase, a lipase, and ascorbate oxidase. The present invention also provides the method for improving the quality of a flour-baked composition, quality improved dough using the same, and quality improved baked composition using the same.

14 Claims, No Drawings

IMPROVING QUALITY OF FLOUR-BAKED COMPOSITIONS

FIELD OF THE INVENTION

This invention relates to a composition for improving the quality of the flour-baked composition (hereinafter also referred to as "quality improver"), the dough composition using the same, a flour-baked composition using the same, a process for producing the flour-baked composition, a method for improving the quality of the flour-baked composition. More particularly, it relates to a food hygienically safe quality improver for a flour-baked composition, such as bread and sponge cake, having sustainable improved texture and taste by use of a safe quality improver, a dough composition using the same, and a process for making the flour-baked composition.

BACKGROUND OF THE INVENTION

Flour-baked compositions, typically bread and sponge cake are made of mainly wheat flour. Such flour-baked compositions usually contain various quality improvers for improving the texture or aroma or for enhancing the mechanical resistance or extensibility of dough.

The quality improver that has been proposed to date include a polyhydric alcohol fatty acid ester type surface active agent, such as a glycerol fatty acid ester, a propylene glycol fatty acid ester, and a sucrose fatty acid ester, combined with ascorbic acid or glucuronolactone (see JP-B-56-42887, JP-A-55-118334, and JP-A-55-118335) (the term "JP-B" as used herein means an "examined Japanese patent publication", and the term "JP-A" as used herein means an "unexamined published Japanese patent application") and a glycerol fatty acid ester having been subjected to a specific treatment (see JP-B-59-41379).

Use of various enzymes or combinations of an enzyme and a quality improver have also been proposed. Examples of known quality improver containing an enzyme include an anti-staling agent for starch products comprising α-starch and/or an extraction residue of defatted soybean and an amylolytic enzyme (see JP-A-54-92641), a bread and cake improver containing glucose oxidase and α-amylase (see JP-A-9-135656), a bread dough improver containing phospholipase A as an active ingredient (see JP-A-59-88040, the text of which is incorporated herein by reference), and a food improver containing specific activated gluten and phospholipase A (see JP-A-61-56037).

Other proposals concerning improvement of flour-baked compositions include, 1) use of an enzymatic decomposition product of wheat gluten as a bread and confection improver (see *Kagaku Kogyo Jiho*, Jun. 25, 1987), 2) proteinous emulsifiers having enhanced effects in quality improvement, such as cereal protein partial decomposition products (see JP-A-1-202234 and JP-A-1-202235), 3) enzymatically decomposed lecithin having quality improving effects on wheat flour (see JP-B-1-55871), 4) starch-based frozen foods having improved quality by addition of a cereal protein partial decomposition product and lecithin (see JP-A-5-252859), and 5) a method of improving quality of flour-baked compositions by addition of a cereal protein partial decomposition product, lecithin, and a sucrose fatty acid ester (see JP-A-8-163953). In particular, JP-A-1-202234 and JP-A-1-202235 suggest a combined use of a cereal protein partial decomposition product with other quality improving components.

However, none of these references teaches that a combination of a cereal protein partial decomposition product and at least one of amylase, lipase, and ascorbate oxidase exhibits marked effects in improving quality of flour-baked compositions.

In the process of making bread from wheat flour, in particular, quality improver (bread improver) are used in combination with other bread raw materials, such as salt, saccharides, dairy products (e.g., skim milk), and so forth for the purpose of making high quality bread, for example, for acceleration of yeast fermentation, water conditioning, improvement of baking properties of the dough, pH adjustment of the dough, and improvement of the texture and aroma. Because use of only one kind of bread improver is inadequate to meet all the requirements, various bread improver have been used in combination.

Such bread improver include yeast food and emulsifiers. Yeast food is added for the purpose of making it easier to produce high quality bread in a stable manner and, more specifically, for the purpose of 1) conditioning water, 2) providing yeast with nutriment, 3) conditioning dough, 4) adjusting the pH of the dough, and 5) supplying enzymes.

Yeast food is classified into an inorganic type containing an inorganic oxidizing agent and minerals such as calcium salts; an organic type mainly containing an enzyme preparation; an organic/inorganic mixed type; and a quick type containing the mixed type yeast food and an increased amount of an oxidizing agent. Ingredients making up these yeast foods include inorganic salts, such as calcium salts, magnesium salts, potassium salts, sodium salts, and ammonium salts; reducing agents, such as ascorbic acid and cysteine; enzymes, such as amylases, proteases, and lipoxygenase; reducing agents, such as glutathione and cysteine; and starch.

The emulsifiers are used to improve the physical properties of baking dough, particularly resistance to mechanized industrial bread making process, and to prevent aging. Conventional emulsifiers include polyhydric alcohol fatty acid ester type surface active agents, such as glycerol fatty acid esters, propylene glycol fatty acid esters, and sucrose fatty acid esters.

Flour-baked compositions such as bread deteriorate in aroma and taste with time after baking. While such staling or aging of bread is ascribed to aging of starch in a narrow sense of the word, but the term "aging" of bread is generally used to mean deterioration of the total bread quality, such as 1) loss of aroma due to dissipation of aromatic components, generation of an unpleasant odor, 2) migration of the water content from the crumb to the crust, and 3) increased hardness and decreased taste due to chemical aging of starch, and the like. On aging, the crumb gets hard and crumbly with bad texture and taste, and the crust becomes hardly chewable like leather due to the water content having migrated from the crumb.

From the consumers' point of view, it has been demanded to use safe food additives, such as quality improver, of, if possible, natural origin (e.g. ascorbic acid or cysteine etc., which is not required to be displayed as an additive) and in minimized amounts. In the field of flour-baked compositions such as bread, it has been urged to reconsider the effects and the necessity of conventionally used quality improver.

SUMMARY OF THE INVENTION

Accordingly, it is an object of the present invention to provide the quality improver, a dough composition using the same, the flour-baked compositions using the same, such as bread and sponge cake, having sustainable improved texture and taste by use of a safe quality improver, a process for making the flour-baked compositions, and method for improving the quality of the flower-baked composition.

Under the above-described circumstances, the present inventors have extensively investigated possible combinations of safe quality improver. As a result, they have found that the above object of the invention is accomplished by a quality improver comprising a specific cereal protein partial decomposition product and at least one enzyme selected from amylases, lipases, and ascorbate oxidase. They have found that this quality improver combined simply with a reducing agent (preferably ascorbic acid or cysteine) as the yeast food, meets all the purposes of adding conventional yeast food and produces improving effects on the physical properties of baking dough and anti-aging effects without addition of an emulsifier. The present invention has been completed based on these findings.

The present invention provides a composition for improving the quality of a flour-baked composition, which comprises:

(a) a cereal protein partial decomposition product having a weight average molecular weight (Mw) of about 5,000 to about 90,000, and (b) at least one enzyme selected from the group consisting of amylase, lipase, and ascorbate oxidase.

The invention also provides a dough composition comprising, 100 parts by weight of flour, 0.005 to 2 parts by weight of ingredient (a) mentioned above, and 1 to 1,500 units of ingredient (b) mentioned above.

The invention further provides a flour-baked composition obtained from a mixture comprising, 100 parts by weight of flour, 0.005 to 2 parts by weight of ingredient (a) mentioned above, and 1 to 1,500 units of ingredient (b) mentioned above.

The invention further provides a process for producing a flour-baked composition, which comprises: adding, based on 100 parts by weight of flour; 0.005 to 2 parts by weight of ingredient (a) mentioned above, and 1 to 1,500 units of ingredient (b) mentioned above; kneading the mixture to prepare dough; and baking said dough.

The invention further provides a method for improving the quality of a flour-baked composition, which comprises adding a composition comprising ingredient (a) and ingredient (b) mentioned above.

The invention further provides use of a composition comprising ingredient (a) and ingredient (b) mentioned above for improving the quality of a flour-baked composition.

In a preferred embodiment, the cereal protein partial decomposition has the ratio of the weight average molecular weight after decomposition (Mw) to that before decomposition (Mo), Mw/Mo, ranging from 0.04 to 0.72.

In a further preferred embodiment, the lipase has phospholipase A2 activity.

In a further preferred embodiment, the flour-baked composition is bread.

The effects produced in the invention cannot be obtained when the ingredient (a) or (b) is used alone. It is considered that such unexpected effects are exhibited based on the synergism of the ingredients (a) and (b). The quality improver of the invention produces not only an emulsifying effect but the effects as yeast food. Therefore, without an emulsifier combined, the quality improver of the invention performs the functions as a dough conditioner to improve the physical properties of dough and also retards staling of flour-baked compositions. Further, the objects of yeast food addition can be achieved simply by adding a reducing agent, such as ascorbic acid or cysteine, in combination.

Furthermore, since the quality improver of the invention is made from naturally occurring substances, the flour-baked compositions of the invention are of high safety and quality.

DETAILED DESCRIPTION OF THE INVENTION

The term "flour" as used herein means cereal powder, preferably wheat powder.

The dough of the present invention is not particularly limited either leavened or unleavened. The dough contains the flour and a liquid for kneading (e.g., water, milk, oils, egg, and so forth), and may further contain other commonly used components.

The flour-baked composition is not particularly limited, and may include, for example, bread, sponge cake, pancake, bun, pie, confection, doughnuts, and so forth, and preferably bread.

The term "bake" used herein is not particularly limited and may include, for example, usual baking, steaming, frying and the like, and preferably usual baking.

The raw materials for flour-baked compositions, such as bread and sponge cake, to which the invention is applied are not particularly limited and include, for example, wheat flour, yeast, sugar, salt, skim milk, shortening, water, fats and oils, and so forth.

The cereal protein partial decomposition product which can be used as component (a) in the invention has a weight average molecular weight of about 5,000 to about 90,000 as measured by gel-permeation chromatography. The ratio of the weight average molecular weight of the cereal protein partial decomposition product (Mw) to that of the cereal protein before being decomposed (Mo) (hereinafter referred to as Mw/Mo ratio) is preferably from 0.04 to 0.72. A cereal protein partial decomposition product having a weight average molecular weight of about 10,000 to about 80,000, particularly about 30,000 to about 70,000, and an Mw/Mo ratio of from 0.24 to 0.56 are preferred for securing the quality improving effects on flour-baked compositions.

If the weight average molecular weight Mw is less than about 5,000, or if the Mw/Mo ratio is less than 0.04, the decomposition product mainly comprises amino acids or oligomers thereof and have poor effects in improving the quality of flour-baked compositions. If Mw exceeds about 90,000, the decomposition product is nearly in an undecomposed state, producing little effect on quality improvement.

The weight average molecular weight of the cereal protein partial decomposition product as referred to herein is the value obtained by gel-permeation chromatography on Sephadex G-75 or G-100 available from Pharmacia using sodium polystyrenesulfonate having a molecular weight of 1,600, 6,500, 16,000, 65,000 and 88,000 as standard substances.

The term "cereal protein" as used herein means the proteins contained in cereals, such as wheat, rye, barley, corn, beans (e.g., soybeans), and buck wheat. Of the proteins contained in these cereals, wheat protein is comprised mainly of glutenin and gliadin and called wheat gluten; and corn protein mainly comprises zein and is generally designated corn gluten.

All these cereal proteins are known substances. A partial decomposition product of the cereal protein can be obtained therefrom by customary procedures, such as separation and extraction. In detail, the cereal protein is decomposed with an alkali, an acid, an enzyme, a reducing agent or an oxidizing agent. The decomposition may be carried out in two or more stages. The process described in JP-A-64-14274 (corresponding to JP-B-6-91793, U.S. Pat. Nos. 5,138,038, 5,273,773, 5,274,079 and European Patent 298419, the text of which are all incorporated herein by references) can be applied, for example.

It is preferred that the cereal protein be processed by a combination of a decomposition treatment with at least one of an acid, an enzyme, an oxidizing agent, and a reducing agent and a decomposition treatment with an alkali. More specifically, the process disclosed in JP-A-64-14274 (JP-B-6-91793) can be employed. A cereal protein partial decomposition product obtained by this process is particularly suitable for carrying out the present invention. It is especially preferred to use a partial decomposition product obtained by a combination of a decomposition treatment with an acid and a decomposition treatment with an alkali.

The amylases which can be used in the invention include α-amylase and β-amylase, both of which exist in wheat. They have amylolytic activity and are widely used in the textile industry (as a desizing agent), the manufacture of saccharides such as glucose, starch syrup, syrup, and edible dextrin, bread making, and the manufacture of alcohol. Commercially available amylases can be used.

The lipases used in the invention are enzymes participating in stepwise hydrolysis of triglycerides into glycerol and fatty acids. They are widely distributed in animals (e.g., pancreatic juice, gastric juice, serum, urine and milk), vegetables (e.g., rape seeds and castor seeds), and microorganisms (e.g., fungi, yeasts, and bacteria (e.g., Mycobacterium tuberculosis)). Of the lipase species those having phospholipase A2 activity are preferred for their improving effects on the quality of flour-baked compositions. Phospholipase A2 is one of the enzymes concerned with lecithin and has hydrolytic action on the fatty acids of phospholipids. Commercially available preparations extracted from swine spleen can be used, for example.

Ascorbate oxidase which can be used in the invention is an enzyme for reducing ascorbic acid to produce dehydroascorbic acid and is widely distributed among various plants. Commercially available preparations extracted from cucumber can be used, for example.

The origin, form and degree of purification of enzymes to be used are not particularly limited.

For obtaining quality improving effects on flour-baked compositions, the cereal protein partial decomposition product (a) and at least one enzyme selected from amylases, lipases and ascorbate oxidase (b) are added in an amount of 0.005 to 2 parts by weight, preferably 0.02 to 0.5 part by weight, and 1 to 1,500 units (as total amount of enzymes), respectively, per 100 parts by weight of flour. Where an amylase, a lipase or ascorbate oxidase is used alone as enzyme (a), it is preferably added in an amount of 10 to 100 units, 5 to 50 units or 5 to 200 units, respectively.

The amylase activity is represented in terms of a unit (U) of the liquefying power measured from a reduction of blue value in iodo-starch reaction using potato starch as a substrate. One unit is defined to be an activity that reduces the blue value (hereinafter the blue value is the decrease % of absorbance at 660 nm) of 10 ml of a 1% by weight starch solution (containing 100 mg of potato starch) by 1% at 40° C. per minute.

The lipase activity is expressed by the activity of releasing free fatty acids from a suspension of 50.0 g of olive oil (Japanese Pharmacopoeia) as a substrate, 50.0 g of an alcoholic surface active agent (Adekatol SO-120, supplied from Asahi Denka Kogyo, K.K.) in 150 ml of purified water at 37° C. per minute. One unit is defined to be an activity that releases 1 micromole of free fatty acids under the above assay conditions.

One unit of phospholipase A2 is defined to be an activity that releases 1 micromole of fatty acids at 40° C. and at pH 8 per minutes from egg yolk (containing about 0.4% by weight of phospholipids per egg yolk).

One unit of ascorbate oxidase is defined to be an activity that oxidizes 1 micromole of ascorbic acid per minute in the reaction between 1 ml of 0.5 mM ascorbic acid (pH 5.6) and 0.1 ml of an enzyme solution at 30° C. for 5 minutes.

The mixture of components (a) and (b) may be a mere mixture of two or more powders where all the components are powder, or the mixture may be in the form of liquid, for example, a solution in a sugar liquid or water. The liquid mixture may be mixed with an excipient, such as a starch hydrolysate, followed by drying into powder.

The mixture can be added directly to the raw material mix for making a flour-baked composition, or can previously be dissolved in water as one of the raw materials of a flour-baked composition, or may be added in any stage in the dough preparation.

The flour-baked compositions according to the present invention include baked foods and foodstuffs made from wheat flour as a main ingredient, such as bread and sponge cake such as Castilla. The invention is particularly suitable for bread making. In making bread, it is recommended to use natural salt as a part or the whole of salt as a raw material. With natural salt there is provided bread having a fine grain structure in the crumb and good appearance.

Unless the effects of the invention are not impaired, the dough and the flour-baked compositions of the invention can contain various other acceptable food additives, such as emulsifiers, e.g., quillaiasaponin and lecithin; thickening stabilizers, e.g., xanthan gum, guar gum, carrageenan, and alginic acid; vegetable proteins, e.g., soybean protein and wheat gluten; processed starch, e.g., phosphoric acid-crosslinked starch, starch hydrolysate, and organic acid-added starch; general α- or β-starch; coloring matter; and flavors. A combined use of processed starch or wheat gluten is particularly preferred for improving the texture and taste.

The present invention will now be illustrated in greater detail with reference to Examples, but it should be understood that the invention is not construed as being limited thereto.

Preparation Example

Preparation of Cereal Protein Partial Decomposition Product

Twenty grams of wheat gluten (available from Wako Pure Chemical Industries, Ltd.) was put in a flask containing 100 g of an aqueous solution of hydrochloric acid (equivalent to 1 g of hydrogen chloride) and stirred at 100° C. for 60 minutes. The reaction mixture was neutralized with sodium hydroxide, and pure water was added thereto to make 200 g. A 100 g portion was put in a flask, 0.5 g of sodium hydroxide added thereto, and the mixture stirred at 100° C. for 60 minutes. The reaction mixture was neutralized with hydrochloric acid and spray dried by means of a spray drier L-8 (produced by Ohkawara Kakoki K. K.) to obtain a powdered preparation. The resulting preparation had a weight average molecular weight Mw of 48,000.

EXAMPLES 1 TO 10 and Comparative Examples 1 TO 8

Preparation of Quality Improver

The powdered preparation obtained in Example 1, amylase ("Spitase", produced by Nagase Biochemicals Ltd.), phospholipase A2 ("Lecitase 10L" by Novo Nordisk Bio-industry Ltd.), and ascorbate oxidase ("ascorbate oxidase AMANO 2" by Amano Pharmaceutical Co., Ltd.) were mixed in a ratio shown in Table 1 below to obtain a quality improving composition, Example 1 to 10 and comparative Example 1 to 8. The mixing ratio in Table 1 is based on 100 parts by weight of wheat flour.

TABLE 1

|  | Partial decomposition product[1] | Amylase | Phospholipase A2[2] | Ascorbate oxidase | Processed Starch | Wheat Gluten |
|---|---|---|---|---|---|---|
| Example |  |  |  |  |  |  |
| 1 | 0.05 | 0.002 | — | — | — | — |
| 2 | 0.05 | — | 0.0015 | — | — | — |
| 3 | 0.05 | 0.001 | 0.001 | — | — | — |
| 4 | 0.01 | 0.001 | 0.001 | — | — | — |
| 5 | 0.2 | — | 0.002 | — | — | — |
| 6 | 0.05 | — | 0.0015 | — | 0.05 | — |
| 7 | 0.05 | — | 0.0015 | — | — | 0.05 |
| 8 | 0.05 | — | — | 0.005 | — | — |
| 9 | 0.05 | — | 0.0015 | 0.005 | — | — |
| 10 | 0.05 | 0.002 | — | 0.005 | — | — |
| Comparative Example |  |  |  |  |  |  |
| 1 | — | 0.01 | — | — | 0.05 | — |
| 2 | — | — | 0.005 | — | — | 0.05 |
| 3 | 0.2 | — | — | — | 0.05 | — |
| 4 | — | 0.005 | 0.002 | — | 0.05 | 0.05 |
| 5 | — | — | 0.005 | — | — | — |
| 6 | — | — | — | 0.005 | — | — |
| 7 | — | 0.002 | — | 0.005 | — | — |
| 8 | — | — | 0.005 | 0.005 | — | — |

Note:
[1]Partial decomposition product of wheat gluten prepared in Preparation Example Test Example 1
Organoleptic Test on Bread Loaves of bread were baked by using the bread improver prepared in Examples and Comparative Examples in accordance with the sponge (70%) and dough process as summarized below. The formulation of raw materials is shown in Table 2. The total amount of wheat flour was 900 g, and the bread improver was added to the sponge mix in an amount corresponding to the weight ratio shown in Table 1.

TABLE 2

|  | Sponge Mix (%) | Dough Mix (%) |
|---|---|---|
| Strong flour | 70.0 | 30.0 |
| Compressed yeast | 2.2 |  |
| Ascorbic acid | 0.005 |  |
| Sugar |  | 5.0 |
| Salt |  | 2.0 |
| Skim milk[1] |  | 2.0 |
| Shortening[2] |  | 5.0 |
| Tap water | 40.0 | 25.5 |

Note:
[1]Available from Meiji Milk Products Co., Ltd.
[2]Nissin Donuts Oil 35, produced by The Nissin Oil Mills, Ltd.

Bread Making Procedure and Conditions
1) Mixing of sponge mix:
   L2' M3'*, mixed in SK Mixer (SK-20)
2) Kneading of sponge mix into sponge: 24° C.
3) Sponge fermentation: 27° C., 80% RH×4 hr.
4) Mixing of sponge and dough mix into dough: L2' M5'*→addition of fat and oil L1' M4' H1'*
5) Kneading of dough: 27° C.
6) Resting of dough: 20 min. (floor time)
7) Dividing of dough into portions: 6 portions each weighing 245 g; mold/dough volumetric ratio=4.2
8) Resting of dough: 20 min. (bench time)
9) Molding:
10) Final fermentation: 38° C., 85% RH×50 min.
11) Baking: 210° C.×35 min.
*: rotating speed (L: low, M: Medium, H: High) and time (min.)

After baking, the loaves were allowed to cool at room temperature for 90 minutes and then each put in a plastic bag and stored at room temperature for 2 days. The stored bread was organoleptically tested by 10 panel members. Judgement was made on a scale of one to ten in an ascending order of quality in terms of softness, freshness, texture, and elasticity. All the points were added up to show overall quality. The results obtained are shown in Table 3 immediately below.

TABLE 3

|  |  | Quality after 2 Days' Storage | | | | |
|---|---|---|---|---|---|---|
|  |  | Softness | Freshness | Texture | Elasticity | Overall Quality |
| Example | 1 | 7 | 8 | 7 | 7 | 29 |
|  | 2 | 9 | 9 | 8 | 8 | 34 |
|  | 3 | 9 | 9 | 9 | 8 | 35 |
|  | 4 | 8 | 9 | 7 | 7 | 31 |
|  | 5 | 9 | 9 | 9 | 9 | 36 |
|  | 6 | 9 | 9 | 10 | 9 | 37 |
|  | 7 | 9 | 9 | 9 | 10 | 37 |
|  | 8 | 8 | 7 | 10 | 10 | 35 |
|  | 9 | 9 | 9 | 10 | 9 | 37 |
|  | 10 | 9 | 9 | 8 | 9 | 35 |
| Comparative Example | 1 | 7 | 5 | 4 | 5 | 21 |
|  | 2 | 7 | 5 | 3 | 6 | 21 |
|  | 3 | 4 | 7 | 7 | 6 | 24 |
|  | 4 | 7 | 5 | 4 | 7 | 23 |
|  | 5 | 7 | 5 | 3 | 4 | 19 |
|  | 6 | 4 | 4 | 6 | 7 | 21 |
|  | 7 | 6 | 5 | 5 | 5 | 22 |
|  | 8 | 6 | 6 | 6 | 6 | 24 |

While the invention has been described in detail and with reference to specific examples thereof, it will be apparent to one skilled in the art that various changes and modifications can be made therein without departing from the spirit and scope thereof.

This application is based on Japanese application No. Hei.10-289537 filed on Oct. 12, 1998, the entire contents of which are incorporated hereinto by reference.

What is claimed is:
1. A dough composition comprising:
  (a) 100 parts by weight of flour,
  (b) 0.005 to 2 parts by weight of a cereal protein partial decomposition product having a weight average molecular weight (Mw) of about 5,000 to about 90,000, and
  (c) 1 to 1,500 units of at least one enzyme selected from the group consisting of amylase, lipase, and ascorbate oxidase, wherein said cereal protein decomposition product has a ratio of weight average molecular weight after decomposition (Mw) to that before decomposition (Mo), Mw/Mo ranging from 0.04 to 0.72.
2. The dough composition as claimed in claim 1, wherein the at least one enzyme is a lipase and wherein said lipase is phospholipase A2.

3. The dough composition as claimed in claim 1, wherein said lipase is phospholipase A2.

4. The dough composition as claimed in claim 1, which further comprises a reducing agent.

5. A flour-containing baked food product obtained by baking a mixture a mixture comprising:
   (a) 100 parts by weight of flour,
   (b) 0.005 to 2 parts by weight of a cereal protein partial decomposition product having a weight average molecular weight (Mw) of about 5,000 to about 90,000, and
   (c) 1 to 1,500 units of at least one enzyme selected from the group consisting of amylase, lipase, and ascorbate oxidase, wherein said cereal protein decomposition product has a ratio of weight average molecular weight after decomposition (Mw) to that before decomposition (Mo), Mw/Mo ranging from 0.04 to 0.72.

6. The flour-containing baked-food product as claimed in claim 5, wherein the at least one enzyme is a lipase and wherein said lipase is phospholipase A2.

7. The flour-containing baked-food product as claimed in claim 5, which is bread.

8. The flour-containing baked-food product as claimed in claim 5, which mixture further comprises a reducing agent.

9. A process for producing a flour-containing baked-food product which comprises:
   adding to a flour-containing dough, based on 100 parts by weight of flour,
   (a) 0.005 to 2 parts by weight of a cereal protein partial decomposition product having a weight average molecular weight (Mw) of about 5,000 to about 90,000, and
   (b) 1 to 1,500 units of at least one enzyme selected from amylase, lipase, and ascorbate oxidase, kneading the mixture to prepare dough, and baking said dough, wherein said cereal protein decomposition product has a ratio of weight average molecular weight after decomposition (Mw) to that before decomposition (Mo), Mw/Mo ranging from 0.04 to 0.72; and
   baking the flour-containing dough.

10. The process as claimed in claim 9, wherein the at least one enzyme is a lipase and wherein said lipase is phospholipase A2.

11. The process as claimed in claim 9, wherein said flour-containing baked food product is bread.

12. The dough composition as claimed in claim 1, wherein said cereal protein decomposition product is produced by a process comprising contacting a cereal protein with one or more selected decomposition agents from the group consisting of an acid, an enzyme, an oxidizing agent, and a reducing agent; and subsequently contacting said cereal protein with an alkali.

13. The flour-containing baked-food product as claimed in claim 5, wherein said cereal protein decomposition product is produced by a process comprising contacting a cereal protein with one or more decomposition agents selected from the group consisting of an acid, an enzyme, an oxidizing agent, and a reducing agent; and subsequently contacting said cereal protein with an alkali.

14. The method as claimed in claim 9, wherein said cereal protein decomposition product is produced by a process comprising contacting a cereal protein with one or more decomposition agents selected from the group consisting of an acid, an enzyme, an oxidizing agent, and a reducing agent; and subsequently contacting said cereal protein with an alkali.

* * * * *